US00PP16287P2

(12) United States Plant Patent
Dekker

(10) Patent No.: US PP16,287 P2
(45) Date of Patent: Feb. 21, 2006

(54) ***CHRYSANTHEMUM* PLANT NAMED 'JEANNY ORANGE'**

(50) Latin Name: *Chrysanthemum×morifolium*
Varietal Denomination: Jeanny Orange

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 11/022,029

(22) Filed: Dec. 24, 2004

(51) Int. Cl.
*A01H 5/00* (2006.01)

(52) U.S. Cl. ..... Plt./290

(58) Field of Classification Search ..... Plt./290
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Jeanny Orange', characterized by its decorative pompon-type inflorescences with elongated oblong-shaped, light orange-colored ray florets; strong and upright flowering stems; freely flowering habit; early and uniform flowering response; and good postproduction longevity.

1 Drawing Sheet

Botanical designation: *Chrysanthemum×morifolium.*
Cultivar denomination: 'Jeanny Orange'.

BACKGROUND OF THE INVENTION

The present invention relates to a new and distinct cultivar of *Chrysanthemum* plant, botanically known as *Chrysanthemum×morifolium* and referred to by the name 'Jeanny Orange'.

The new *Chrysanthemum* is a naturally-occurring whole plant mutation of a proprietary selection of *Chrysanthemum×morifolium* identified as code number 00.4758,04, not patented. The new *Chrysanthemum* was discovered and selected by the Inventor on Sep. 20, 2002 as a single flowering plant within a population of plants of the parent selection in a controlled environment in Hensbroek, The Netherlands.

Asexual reproduction of the new *Chrysanthemum* by terminal cuttings in Hensbroek, The Netherlands since 2002, has shown that the unique features of this new *Chrysanthemum* are stable and reproduced true to type in successive generations.

BRIEF SUMMARY OF THE INVENTION

The cultivar Jeanny Orange has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Jeanny Orange'. These characteristics in combination distinguish 'Jeanny Orange' as a new and distinct cultivar:

1. Decorative pompon-type inflorescences with elongated oblong-shaped, light orange-colored ray florets; typically grown as a spray-type.
2. Strong and upright flowering stems.
3. Freely flowering habit.

4. Early and uniform flowering response.
5. Good postproduction longevity.

Plants of the new *Chrysanthemum* can be compared to plants of the parent selection. In side-by-side comparisons conducted in Hensbroek, The Netherlands, plants of the new *Chrysanthemum* differed primarily from plants of the parent selection in ray floret coloration as plants of the parent selection had pink-colored ray florets.

Plants of the new *Chrysanthemum* can be compared to plants of the *Chrysanthemum* cultivar Yoko Ono, disclosed in U.S. Plant Pat. No. 12,566. In side-by-side comparisons conducted in Hensbroek, The Netherlands, plants of the new *Chrysanthemum* differed primarily from plants of the cultivar Yoko Ono in the following characteristics:

1. Plants of the new *Chrysanthemum* were more vigorous than plants of the cultivar Yoko Ono.
2. Plants of the new *Chrysanthemum* had larger and stronger leaves than plants of the cultivar Yoko Ono.
3. Plants of the new *Chrysanthemum* had larger inflorescences with more ray florets per inflorescence than plants of the cultivar Yoko Ono.
4. Plants of the new *Chrysanthemum* and the parent selection differed in ray floret coloration as plants of the cultivar Yoko Ono was green.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering stem of 'Jeanny Orange'.

The photograph at the bottom of the sheet comprises a close-up view of upper and lower surfaces of typical inflorescences and typical leaves of 'Jeanny Orange'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the summer and autumn in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5 to 30° C., night temperatures ranged from 18.5 to 24° C. and light levels were about five kilolux. Plants were pinched once and were about ten weeks from planting when the photographs and the description were taken.

Botanical classification: *Chrysanthemum×morifolium* cultivar Jeanny Orange.

Commercial classification: Decorative pompon-type *Chrysanthemum* typically grown as a spray-type cut flower.

Parentage: Naturally-occurring whole plant mutation of a proprietary selection of *Chrysanthemum×morifolium* identified as code number 00.4758,04, not patented.

Propagation:

*Type.*—Terminal tip cuttings.

*Time to initiate roots, summer.*—About 6 days at 20° C.

*Time to initate roots, winter.*—About 7 days at 20° C.

*Time to produce a rooted cutting, summer.*—About 14 days at 20° C.

*Time to produce a rooted cutting, winter.*—About 16 days at 20° C.

*Root description.*—Fine and freely branching; light brown in color.

Plant description:

*Appearance.*—Herbaceous decorative pompon-type cut *Chrysanthemum*; typically grown as a spray-type; erect and strong flowering stems. Moderately vigorous.

*Flowering stem description.*—Length: About 70 to 80 cm. Diameter: About 6 mm. Strength: Strong. Texture: Pubescent. Aspect: Erect. Branching habit: Plants are typically grown as single stems. Color: 146C.

*Foliage description.*—Arrangement: Alternate. Length: About 8 to 10 cm. Width: About 7 to 8 cm. Apex: Cuspidate. Base: Attenuate. Margin: Pinnately lobed. Texture, upper and lower surface: Pubescent; rough. Petiole length: About 2 to 3.5 cm. Color: Developing and fully expanded foliage, upper surface: 147A. Developing and fully expanded foliage, lower surface: Closest to 147B. Venation, upper and lower surfaces: 146C. Petiole, upper and lower surfaces: 146C.

Inflorescence description:

*Appearance.*—Decorative pompon-type inflorescence form with elongated oblong-shaped ray florets. Inflorescences borne on terminals above foliage. Disk and ray florets develop acropetally on a capitulum. Inflorescences not fragrant. Typically grown as a spray-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 7.5 weeks later. Early and uniform flowering response.

*Postproduction longevity.*—Cut inflorescences will maintain good substance and form for about three weeks.

*Quantity of inflorescences per flowering stem.*—About 13 to 18 inflorescences per flowering stem.

*Inflorescence size.*—Diameter: About 3 to 4 cm. Depth (height): About 1.5 to 2 cm. Diameter of disc: About 3 mm.

*Inflorescence buds.*—Height: About 4 to 6 mm. Diameter: About 1 to 1.3 cm. Shape: Oblate. Color: 138B.

*Ray florets.*—Length: About 7 to 18 mm. Width: About 2 to 8 mm. Shape: Elongated oblong; incurving. Apex: Rounded. Base: Fused; tubular. Margin: Entire. Texture, upper and lower surfaces: Smooth, glabrous. Number of ray florets per inflorescence: About 450 in numerous whorls. Color: When opening, upper and lower surfaces: 150C. Fully opened, upper surface: 14B to 14C; color becoming closer to 14C with development. Fully opened, lower surface: 14D.

*Disc florets.*—Shape: Tubular; elongated. Length: About 2 mm. Width: About 1 mm. Number of disc florets per inflorescence: About 12. Color, immature and mature: 144B.

*Peduncles.*—Length, terminal peduncle: About 5.5 cm. Length, fourth peduncle: About 9 cm. Diameter: About 2 to 3 mm. Angle: About 45° from vertical. Strength: Moderately strong. Texture: Pubescent. Color: 146B.

*Reproductive organs.*—Androecium: Present on disc florets only. Anther color: 151B. Pollen color: 23A. Gynoecium: Present on both ray and disc florets. Stigma length: About 1 mm. Stigma diameter: About 0.3 mm. Stigma color: Towards the apex, 151B; towards the base, 144C to 144D.

*Seed/fruit.*—Seed and fruit production has not been observed.

Disease/pest resistance: Resistance to known *Chrysanthemum* pathogens and pests has not been observed on plants of the new *Chrysanthemum.*

It is claimed:

1. A new and distinct cultivar of *Chrysanthemum* plant named 'Jeanny Orange', illustrated and described.

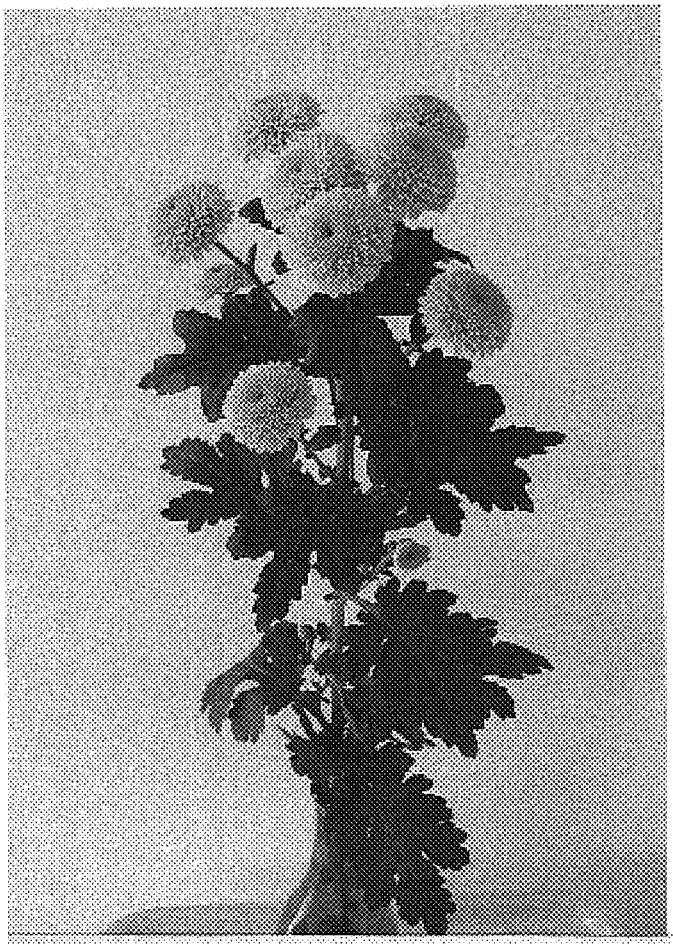
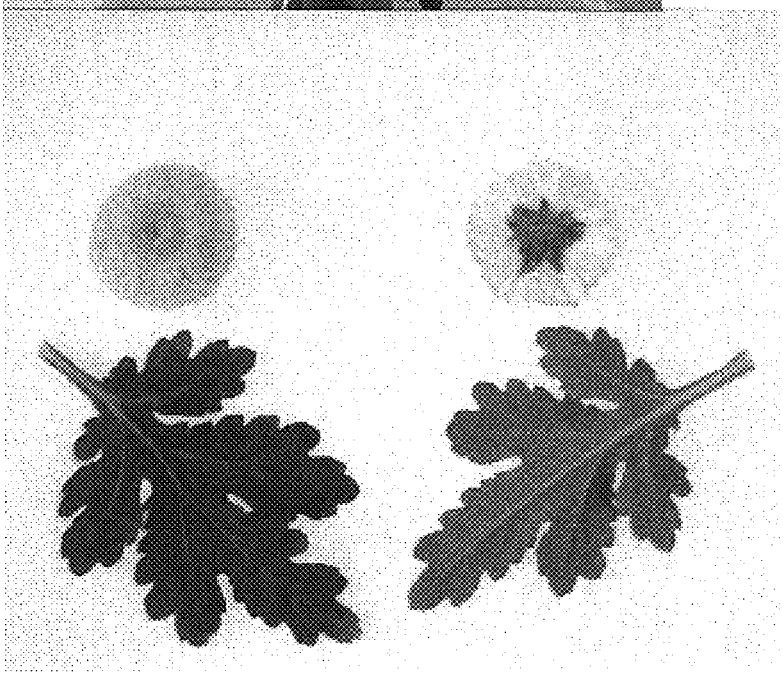

* * * * *